United States Patent [19]

Seifert et al.

[11] 4,182,917

[45] Jan. 8, 1980

[54] PROCESS FOR THE PREPARATION OF POLYHYDRIC PHENOLS

[75] Inventors: Hermann Seifert, Cologne; Helmut Waldmann; Wulf Schwerdtel, both of Leverkusen; Wolfgang Swodenk, Odenthal, all of Fed. Rep. of Germany

[73] Assignee: Bayer Aktiengesellschaft, Leverkusen, Fed. Rep. of Germany

[21] Appl. No.: 857,622

[22] Filed: Dec. 5, 1977

[30] Foreign Application Priority Data

Dec. 24, 1976 [DE] Fed. Rep. of Germany ....... 2658943

[51] Int. Cl.$^2$ ............................................. C07C 39/08
[52] U.S. Cl. ................................................. 568/771
[58] Field of Search .......................... 260/621 G, 625; 568/771

[56] References Cited

U.S. PATENT DOCUMENTS

| 3,950,437 | 4/1976 | Imamura et al. ................ 260/621 G |
| 4,066,707 | 1/1978 | Nakatani et al. ................ 260/621 G |

FOREIGN PATENT DOCUMENTS 1479354   3/1966   France ............................... 260/621 G

*Primary Examiner*—Werren B. Lone
*Attorney, Agent, or Firm*—Sprung, Felfe, Horn, Lynch & Kramer

[57] ABSTRACT

A process has been invented for the preparation of pyrocatechol and hydroquinone which comprises reacting a solution which is substantially anhydrous and free from hydrogen peroxide, of a percarboxylic acid in an inert, organic solvent, with phenol at temperatures from −10° C. to 80° C.

The compounds obtained according to the invention are known, important industrial chemicals which are used in large amounts in the field of photography and of dyestuffs and plastics and in the field of scents and flavorings.

20 Claims, No Drawings

PROCESS FOR THE PREPARATION OF POLYHYDRIC PHENOLS

The present invention relates to an improved process for the preparation of polyhydric phenols.

Polyhydric phenols, such as the dihydric phenols pyrocatechol and hydroquinone, are important industrial intermediate products which are used in large amounts in the field of photography and of dyestuffs and plastics and in the field of scents and flavourings.

In accordance with the great industrial importance of these compounds, in the past there has been no lack of numerous attempts to discover simple processes for the preparation of pyrocatechol and hydroquinone which enable these compounds to be prepared on an industrial scale avoiding intermediate stages and by-products which pollute the environment.

Thus, for example, the dihydric phenols pyrocatechol and hydroquinone, which are derived from benzene, are today prepared industrially by processes which proceed via various intermediate stages (K. Weissermel and H. J. Arpe "Industrielle organische Chemie" ("Industrial Organic Chemistry") (Verlag Chemie) Weinheim 1976, page 298-302). In order to obtain hydroquinone, for example, benzene must first be nitrated, after which the corresponding intermediate stage, that is to say nitrobenzene, is reduced to aniline. The aniline is then in turn reacted with manganese dioxide in aqueous sulphuric acid to give p-benzoquinone ("Ullmanns Enzyklopädie der technischen Chemie" ("Ullmann's Encyclopaedia of Industrial Chemistry"), volume 8, (Urban and Schwarzenberg), Munich 1957, page 741) and this is reduced to hydroquinone.

In order to prepare pyrocatechol, phenol is reacted with chlorine to give 2-chlorophenol and this is subjected to alkali fusion, an alkali metal chloride being obtained as a by-product which pollutes the environment (Louis F. Fieser and M. Frieser "Organische Chemie" (Organic Chemistry"), (Verlag Chemie) Weinheim 1965, page 915). A further process for the preparation of pyrocatechol uses phenol-o-sulphonic acid as the intermediate stage, which must also be subjected to alkali fusion (Carl R. Noller, "Lehrbuch der organischen Chemie" ("Textbook of organic Chemistry"), (Springer Verlag) Berlin 1960, page 545).

More recent processes attempt to introduce the second hydroxyl group into the phenol directly by means of hydrogen peroxide, avoiding intermediate stages. However, catalysts are required for this reaction between hydrogen peroxide and phenol in order to activate the hydrogen peroxide. In processes in which metal salts, preferably salts of transision metals, are used as the catalyst, there is always the danger that oxidation of the aromatic ring, which proceeds further and leads as far as quinones or other conversion products of phenol, occurs as a side reaction which considerably lowers the industrial value of these processes.

In addition, there is also the danger that these heavy metal ions have a decomposing action on the hydrogen peroxide (H. Remy, "Lehrbuch der anorganischen Chemie" ("Textbook of inorganic Chemistry"), volume I, 11th edition, (Geest and Portig) Leipzig 1960, page 71). Satisfactory yields of polyhydric phenols are only obtained in a procedure which excludes an industrial application. Thus, A. Chwala and co-workers (J. Prakt. Chem. 152, 46 (1939) could obtain the dihydric phenols pyrocatechol and hydroquinone in 72% yield in the reaction of phenol with hydrogen peroxide in a very dilute, aqueous solution containing sulphuric acid, using iron sulphate as the catalyst. However, very long reaction times and a reaction temperature of 0° C. were necessary for this. In addition, carrying out the process in a very dilute, aqueous medium entails considerable difficulties in isolating the dihydric phenols from the reaction mixture.

In a further process, the industrial utilisation of which would present considerable difficulties, the use of strong acids as the catalyst for the reaction of phenol with hydrogen peroxide is proposed, according to German Auslegeschrift (German Published specification No.) 2,064,497. In this procedure, however, in order to achieve yields of about 70%, relative to the hydrogen peroxide employed, it is necessary to employ the aqueous $H_2O_2$ in concentrations above 90%. The use of such high concentrations of $H_2O_2$ is associated with the danger of explosion and necessitates extensive and expensive safety measures in the case of an industrial process. A further disadvantage of this process is that the problem of the separation of the acid, used as the catalyst, from the reaction mixture is not satisfactorily solved in the sense of an industrial application. In the process according to German Auslegeschrift (German Published specification No. ) 2,064,497, an equimolar amount of water is also formed from the hydrogen peroxide during the reaction and this makes the separation of the phenol employed in excess difficult, because of the azeotrope water/phenol, and leads to effluents containing phenol, which can be purified only with considerable technical effort.

According to German Patent specification No. 1,543,830, it should be possible to avoid the difficulties which occur when working with highly concentrated aqueous hydrogen peroxide if hydrogen peroxide is used, for introducing a hydroxyl group into the ring of aromatic compounds, as a very dilute organic solution in the presence of boric acid or boric acid derivatives and if the resulting boric acid esters of the hydroxylated aromatic compounds are then saponified. However, using boric acid derivatives as hydrogen peroxide activators results in the corresponding boric acid esters first being formed from the hydroxylated aromatic compounds during the reaction, and these must then be saponified in a subsequent process step. The expense connected with this is the decisive disadvantage of this process. The separation and regeneration of the hydrogen peroxide activator containing boron is also expensive.

Substantial improvements in the hydroxylation of phenolic compounds by means of hydrogen peroxide could be achieved, according to German Offenlegungsschrift (German Published specification No.) 2,410,758, by carrying out the reaction of the phenolic compound with non-aqueous hydrogen peroxide, dissolved in an organic solvent or in the phenol, to be hydroxylated, itself, in the presence of catalytic amounts of a strong acid. However, this process also has the fundamental disadvantages of a process which is carried out in the presence of a strong mineral acid. Such disadvantages are to be seen essentially as the complications in separating off the strong mineral acid from the reaction mixture.

Attempts to achieve a process for hydroxylating phenol with hydrogen peroxide without the aid of a mineral acid have already been indicated a very long time ago. Thus, G. G. Henderson and co-workers have attempted (J. Chem. Soc. (London) 97, 1659 (1910)) to introduce further hydroxyl groups into phenols by reaction with hydrogen peroxide/acetic acid. In the case of phenol itself, a reaction time of several days at room temperature was necessary in order to obtain a mixture of hydroquinone, pyrocatechol and p-benzoquinone. Very long reaction times were also required to introduce three further hydroxyl groups into the aromatic nucleus of p-tert.-butylphenol. From this publication it can be seen, in particular, that an excess of hydrogen peroxide and temperatures above room temperature had to be strictly avoided.

In German Auslegeschrift (German Published specification No.) 1,593,968 it is proposed to carry out the introduction of a further hydroxyl group into phenol with a percarboxylic acid prepared in situ from aqueous hydrogen peroxide and a carboxylic acid in the presence of phosphoric acid, formic acid/$H_2O_2$ mixtures and acetic acid/$H_2O_2$ mixtures preferably being used. Since hydrogen peroxide is employed in the process as an aqueous solution, the raction mixture to be worked up after the conversion contains amounts of water which are not insignificant. This amount of water introduced into the reaction mixture with the hydrogen peroxide is additionally also increased by the amount of water which is formed during the in situ formation of the percarboxylic acid from the carboxylic acid and hydrogen peroxide according to equation (1).

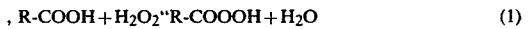

$$, R\text{-}COOH + H_2O_2 \rightleftharpoons R\text{-}COOOH + H_2O \qquad (1)$$

Thus, when the $H_2O_2$ is completely converted, equimolar amounts of water corresponding to the hydrogen peroxide employed in the reaction are formed and are also contained in the reaction mixture after the reaction has ended. As already mentioned, the presence of water makes the separation of the phenol present in excess in the reaction according to the process of DAS (German Published specification No.) 1,593,968 difficult as a result of azeotrope formation, whereby this separation becomes very expensive industrially, in particular when the phenol thus obtained is to be recycled to the reaction, which is usually necessary in practice.

However, the difficulties caused by the formation of azerotropic mixtures can already occur in the separation, by distillation, of the carboxylic acid, which has a lower boiling point than phenol, since, as is known, low-molecular carboxylic acids, such as, for example, formic acid and acetic acid, also form azeotropes with water (Robert C. Weast (Editor), "Handbook of Chemistry and Physics", 53rd edition, (The Chemical Rubber Company) Cleveland/Ohio 1972, page D-2 and D-25). In this case also, it is extremely difficult to dehydrate the carboxylic acid industrially in order to be able to re-use it in a suitable form for the reaction with the phenol and the $H_2O_2$.

Moreover, the working up of the reaction mixture obtained by the process of German Auslegeschrift (German Published specification No.) 1,593,968 is also made considerably difficult by the fact that the phosphoric acid used to achieve yields of, for example, 67% must be removed again from the reaction mixture by employing an anion exchanger resin, such as is proposed in DT-AS (German Published specification No.) 1,593,968, or by another, additional process step. Moreover, the required reaction times, which are three and more hours at a temperature of 80° C., and the yields of only 54–67% of dihydric phenols, such as can be seen from Examples 1 to 3 of DT-AS (German Published specification No.) 1,593,968, signify considerable disadvantages for an industrial preparation of dihydric phenols by this process.

A further disadvantage of the process of DT-AS German Published specification No.) 1,593,968 is that the formic acid used for introducing a hydroxyl group into the phenol (the highest yields, in connection with the use of phosphoric acid, are only achieved with this acid (compare Examples 1 and 2 of DT-AS (German Published specification No.) 1,593,968)), occupies a special position amongst the carboxylic acids with respect to the corrosion problem, which is always of considerable importance in reactions with lower carboxylic acids, because formic acid has a particularly corrosive action, even towards stainless steels.

Summarising, it can be established from the literature on processes for the preparation of polyhydric phenols which has been disclosed hitherto, that all the known processes, including the processes in which percarboxylic acids are used for introducing a further hydroxyl group into phenol, are not able to offer a satisfactory solution to the problem set by industrial requirements and the question of profitability.

Accordingly, it has now been found, surprisingly, that the hydroxylation of phenol to pyrocatechol and hydroquinone can be carried out in a simple manner which is advantageous industrially and economically, when a solution, which is substantially anhydrous and free from hydrogen peroxide, of a percarboxylic acid in an inert, organic solvent is reacted with phenol at temperatures from −10° C. to 80° C.

In general, the anhydrous solution, used for the process according to the invention, of the percarboxylic acid contains not more than about 5% by weight of water. Solutions of percarboxylic acids which contain less than about 3% by weight of water are preferably suitable. Solutions of percarboxylic acids in an inert organic solvent, the water content of which is below 1% by weight, are particularly preferably used. Solutions which contain not more than 0.5% by weight of water are very particularly preferred.

In general, the content of free hydrogen peroxide in the organic solutions of the percarboxylic acid which are suitable for the process according to the invention is not more than 2% by weight. Solutions which contain less than 1% by weight of hydrogen peroxide are preferably employed. Organic solutions which contain less than 0.5% by weight of $H_2O_2$ are very particularly preferred.

Organic solutions of percarboxylic acids, which are suitable for the process according to the invention, still contain small amounts of the acid catalyst from the acid-catalysed preparation and in general contain less than 1% by weight of a free strong acid or of a salt of these acids, such as, for example, sulphuric acid, metanesulphonic acid, trifluoromethanesulphonic acid, perchloric acid or sulphonic acids of benzene or of naphthalene. Solutions with a content of strong acid of less than 0.5% by weight are particularly suitable. Organic solutions of percarboxylic acids which contain less than 0.1% by weight of strong acid are very particularly suitable.

Organic solutions of percarboxylic acids, which are suitable for the process according to the invention, can also contain free carboxylic acid in addition to the percarboxylic acid. The amount of carboxylic acid which can be present in addition to the percarboxylic acid is not important in the process according to the invention. It can be larger or smaller than the amount of percarboxylic acid in the solution. However, in general solutions in which the amount of carboxylic acid is less than that of the percarboxylic acid are reacted with the phenols. The content of carboxylic acid in the percarboxylic acid solution is, for example, about 1 to 50, preferably about 5 to 40, % by weight.

In some cases it can be advantageous to add a stabiliser to the organic solution, which is anhydrous and free from hydrogen peroxide, of the percarboxylic acid. Stabilisers which can be used are carboxylic acids or polycarboxylic acids containing nitrogen or hydroxyl groups, but also phosphorus compounds, such as, for example, the sodium salts of polyphosphoric acids which are partially esterified with long-chain alcohols (compare D. Swern "Organic Peroxides", volume 1, page 350, 1st paragraph; Wiley-Interscience 1970). However, in most cases a stabiliser is not necessary since a substantial decomposition of the percarboxylic acid which impairs the process does not occur at the temperatures at which the process according to the invention is carried out. There is also an advantage to be seen in this, since in the end the stabiliser is an impurity in the reaction mixture.

The concentration of the percarboxylic acid in the organic solution used in the reaction with the phenol can vary within wide limits. In general, concentrations of about 3 to 60% by weight are suitable. Solutions which contain about 5 to 50% be weight of percarboxylic acid are preferably used, and those which have a content of 10 to 30% by weight of percarboxylic acid are very particularly preferred.

Percarboxylic acids which are suitable for the process according to the invention are those which are derived from aliphatic (particularly alkanoic), cycloaliphatic (particularly cycloalkanoic) and aromatic (particularly monocyclic and bicyclic carbocyclic aromatic)-monocarboxylic or dicarboxylic acids. Examples of possible aliphatic carboxylic acids, the percarboxylic acids of which can be used for the process according to the invention, are: formic acid, acetic acid, propionic acid, butyric acid, isobutyric acid, valeric acid, trimethylacetic acid, caproic acid, heptylic acid, caprylic acid, pelargonic acid, capric acid, undecanoic acid, lauric acid, myristic acid, pentadecanoic acid, palmitic acid, stearic acid, arachic acid, fluoracetic acid, trifluoroacetic acid, chloroacetic acid, dichloroacetic acid, trichloroacetic acid, α-chloropropionic acid, α-fluoropropionic acid, β-chloropropionic acid, succinic acid, glutaric acid, adipic acid, suberic acid, azelaic acid and sebacic acid. Cycloaliphatic carboxylic acids which may be mentioned which are a suitable starting material for appropriate percarboxylic acids are cyclopentanecarboxylic acid, cyclohexanecarboxylic acid, cycloheptanecarboxylic acid, cyclohexane-1,3-dicarboxylic acid and cyclohexane-1,4-dicarboxylic acid. Suitable aromatic carboxylic acids for the appropriate percarboxylic acids are benzoic acid, p-chlorobenzoic acid, phthalic acid, naphthalene-carboxylic acid, benzene-1,3-dicarboxylic acid and benzene-1,4-dicarboxylic acid.

Percarboxylic acids which are derived from aliphatic (particularly alkane) carboxylic acids with 2 to 5 carbon atoms, such as acetic acid, propionic acid, n-butyric acid, isobutyric acid and valeric acid or trimethylacetic acid and dimethylpropionic acid, are particularly suitable for the process according to the invention. Propionic acid, and thus perpropionic acid, is very particularly suitable.

Suitable solvents for the solution of the percarboxylic acid, used for introducing a further hydroxyl group into the aromatic nucleus of the phenol, are all the organic solvents which are inert towards the percarboxylic acid. Examples which prove suitable are aromatic (particularly carbocyclic aromatic) hydrocarbons which contain six to ten carbon atoms, aliphatic or cycloaliphatic hydrocarbons, in each case containing up to twelve carbon atoms, chlorinated hydrocarbons (such as chlorinated alkanes) which contain one to ten carbon atoms and one to four chlorine atoms, and esters of carboxylic acids (particularly alkyl esters of alkane carboxylic acids), containing one to five C atoms, with straight-chain or branched alcohols in which one to eight C atoms are present in the molecule, as well as ethers which contain up to ten C atoms. Examples of suitable solvents which may be mentioned are: benzene, toluene, xylene, n-pentane, isooctane, cyclohexane, methylene chloride, chloroform, 1,2-dichloroethane, 1,2-dichloropropane, methyl acetate, ethyl acetate, n-propyl acetate, isopropyl acetate, n-butyl acetate, isoamyl acetate, methyl propionate, ethyl propionate, propyl propionate and butyl propionate, as well as chlorobenzene and ether. However, it is also possible to use mixtures of the solvents mentioned as solvents for the percarboxylic acids, the components of the mixture then being advantageously chosen so that they have a similar boiling point. Chlorinated hydrocarbons, such as methylene chloride, dichloroethane or dichloropropane, aromatic hydrocarbons, such as benzene, or ethers, such as diisopropyl ether, or mixtures of these solvents are preferably used. Benzene is very particularly preferred as the solvent for the process according to the invention.

In general, a percarboxylic acid, the corresponding carboxylic acid of which has a lower boiling point than phenol, and a solvent which has a boiling point which is either lower than the boiling point of the carboxylic acid corresponding to the percarboxylic acid or which is between the boiling point of phenol and that of the carboxylic acid are used for the process according to the invention. However, it is also possible to choose the solvent and carboxylic acid so that both the solvent and the carboxylic acid have higher boiling points than phenol. However, it is advantageous, especially when phenol is employed in excess in the reaction with the organic solution of the percarboxylic acid, to choose the carboxylic acid and solvent so that they both have boiling points below that of the dihydric phenols pyrocatechol and hydroquinone formed during the reaction. A percarboxylic acid, the corresponding carboxylic acid of which has a boiling point, under normal pressure, which is at least 10° C., particularly preferably at least 30° C., below the boiling point of phenol is preferably used in the process according to the invention. Amongst the compounds already listed, a solvent which has a boiling point, under normal pressure, at least 10° C. above or at least 10° C. below, particularly preferably at least 20° C. below, the boiling point of the carboxylic acid corresponding to the percarboxylic acid is preferably chosen as the inert solvent for the percarboxylic acid.

In addition, the percarboxylic acid, or the carboxylic acid corresponding to this, and the solvent for the process according to the invention are advantageously chosen so that no pronounced azeotrope of binary or ternary nature occurs within the combination carboxylic acid/solvent/phenol.

The solution, which is anhydrous and free from hydrogen peroxide, of the percarboxylic acid in the inert organic solvent can be prepared in a manner which is in itself known. Thus, a solution of this type can be obtained by oxidising an aldehyde to the corresponding percarboxylic acid using oxygen or oxygen-containing gases. However, it is also possible to subject an ester of a carboxylic acid with an alcohol which has a lower boiling point than the inert organic solvent to a perhydrolysis with hydrogen peroxide and thereafter to distill off the alcohol formed and the water. The organic solution of the percarboxylic acid is obtained in a manner which is advantageous industrially, for example according to the process of German Patent specification No. 2,262,970, by extracting a reaction mixture, contained by reacting hydrogen peroxide, water, an acid catalyst and a carboxylic acid, with the inert organic solvent and, if appropriate, subsequently drying the extract, which essentially contains the percarboxylic acid.

The phenol, which, by the process according to the invention, is subjected to the reaction with the anhydrous organic solution of the percarboxylic acid should have a water content which is as low as possible. In general, it is sufficient if the content of water is less than 2% by weight. A phenol which contains less than 1% by weight of water is preferably used.

The phenol can be reacted with the organic solution of the percarboxylic acid in the form of a solution. However, it is also possible to react pure phenol with the percarboxylic acid solution. If the phenol is employed in solution, the solvent in which the percarboxylic acid is dissolved is preferably chosen. The phenol being reacted is itself particularly preferably used as the solvent.

The ratio of percarboxylic acid to the phenol being reacted can vary within wide limits. It can be chosen so that the molar amount of phenol to be hydroxylated is about 1 to 50 mols, relative to one mol of percarboxylic acid employed in the reaction. In general, it is advantageous to choose a ratio of 5 to 30 mols of phenol per mol of percarboxylic acid.

The temperatures at which the hydroxylation, by the process according to the invention, of phenol to pyrocatechol and hydroquinone by reacting the phenol with an organic solution of the percarboxylic acid is carried out, are about $-10°$ C. to about 80° C., preferably about 0° C. to 45° C., particularly preferably 20° C. to 45° C.

The pressure is not decisive for the reaction. In principle, the reaction can be carried out under elevated pressures, under normal pressure or also under reduced pressure. All or some of the reactants can be present in the gaseous form. In order to remove the heat of reaction, the mixture can be cooled with a suitable medium. In order to set the desired reaction temperature exactly, the pressure in the reaction vessel is chosen, for example, so that the reaction mixture just boils. Devices which are customary for conversions of this type can be used for carrying out the reaction, such as stirred kettles, tube reactors or loop reactions. In general, when the reaction is carried out continuously, a device which behaves as a cascade of at least two ideally mixed kettles is used. It is particularly advantageous to use a reaction system which behaves as a cascade of 4 to 50, preferably 10 to 30, ideally mixed kettles. However, it is also possible to carry out the reaction discontinuously. Suitable materials from which the devices for carrying out the reaction can be manufactured are glass, enamel or alloyed stainless steel.

The reaction time depends on the temperature and the concentration of the percarboxylic acid and of the phenol as well as of the solvent in which the percarboxylic acid is employed. As a rule, the reaction conditions are chosen such that the reaction proceeds so that the percarboxylic acid is converted to the extent of over 98% after 10 to 90 minutes, preferably after 15 to 60 minutes, particularly preferably after 20 to 45 minutes.

The reaction mixture is worked up by customary methods, for example by fractional distillation in vacuo, the solvent for the percarboxylic acid being initially recovered in a first stage and thereafter the carboxylic acid corresponding to the percarboxylic acid being recovered in a second distillation unit. Thereafter, if phenol has been employed in excess in the reaction, the phenol is first recovered and then the dihydric phenols are isolated. However, it is also possible first to separate off the solvent and the carboxylic acid by distillation and thereafter to obtain pyrocatechol and hydroquinone by fractional crystallisation. The reaction mixture can also be worked up by extraction or by a combination of the extraction process and distillation process.

The carboxylic acid recovered and the organic solvent recovered during the working up of the reaction mixture are advantageously re-used for the preparation of the organic solution of the percarboxylic acid. The phenol which may be recovered during the working up is preferably recycled to the reaction with the percarboxylic acid, if appropriate after intermediate purification, but can also be employed in another application.

In a particular embodiment of the process according to the invention, a solution, which is non-aqueous and essentially free from hydrogen peroxide and which contains 10 to 35% by weight of perpropionic acid and 5 to 25% by weight of propionic acid, of perpropionic acid in benzene or dichloropropane is added to a solution, which is stirred and warmed to 20° C. to 50° C. and which contains 20 to 80% by weight of phenol, of phenol in benzene or dichloropropane, or to the melt of the phenol, in such a way that the temperature can be kept within the range indicated. The perpropionic acid solution being reacted with the phenol contains less than 1% by weight of water and 0.1 to 0.8% by weight of free hydrogen peroxide. The molar ratio of phenol to perpropionic acid is 5 to 25:1. The time required for the addition of the solution of the perpropionic acid is 3 to 30 minutes. After 10 minutes to 2 hours, calculated from the end of the addition of the solution, the perpropionic acid is converted to the extent of more than 98%. The selectivity for pyrocatechol and hydroquinone (determined, for example, by analysis of the reaction mixture, after cooling, by gas chromatography) is 85 to 95% relative to the perpropionic acid employed in the reaction. The ratio of pyrocatechol to hydroquinone is 1.1–2.5 parts by weight.

After distilling off the solvent and the propionic acid under 500 to 100 mm Hg, the excess phenol is recovered by a further rectification step, also carried out under reduced pressure, after which the mixture of the two diphenols pyrocatechol and hydroquinone, which now remains and which contains small amounts of higher-boiling impurities, is separated into the components, which separation can be carried out by fractional distillation in vacuo or by crystallisation.

EXAMPLE 1

188 g (≙2 mols) of phenol are introduced into a reaction vessel, fitted with a reflux condenser, stirring device and dropping funnel, and are warmed to a temperature of 41° C. 48.8 g of a 20.6% strength by weight solution of perpropionic acid in benzene, which also contains 13.4% by weight of propionic acid, 0.22% by weight of hydrogen peroxide and 0.15% by weight of water in addition to the perpropionic acid, are added dropwise to the liquid phenol in the course of 12 minutes, whilst stirring, the temperature of the reaction mixture being kept at 40 to 42° C., which is achieved by appropriately controlling the removal of heat. After a further reaction time of 25 minutes, the conversion of perpropionic acid is determined as 98.7%. At the same time, 7.0 g of pyrocatechol and 4.37 g of hydroquinone are found in the reaction mixture, which corresponds to a selectivity for both diphenols of 92.6%, relative to the perpropionic acid employed in the reaction. The amount of phenol recovered from the reaction mixture is 177.3 g.

EXAMPLE 2

106 g of a benzene solution containing 25.3% by weight of perisobutyric acid, which was prepared according to the instructions of W. M. Weigert et al., Chemiker-Zeitung 99 (1975) 107, are added to 560 g of a solution, warmed to 25° C., of phenol in dichloropropane, which contains 67% by weight of phenol, in the course of 15 minutes, whilst stirring. In addition to the perisobutyric acid, this benzene solution contains 17.2% by weight of isobutyric acid, 0.3% by weight of water and 0.23% by weight of hydrogen peroxide.

During the addition of the perisobutyric acid solution to the solution of phenol in dichloropropane, the temperature rises to 34° C. After the addition of the solution of perisobutyric acid has ended, the temperature of the reaction mixture is adjusted to 30° C., after which the mixture is stirred for a further 40 minutes at this temperature in order to bring the conversion to completion. After this time, the perisobutyric acid has been converted to the extent of 99.2%. A total of 25.72 g of dihydroxybenzenes are determined in the reaction mixture by means of analysis of gas chromatography, which corresponds to a yield of these products of 90.8%, relative to the perisobutyric acid employed in the reaction. The ratio of pyrocatechol to hydroquinone is 1.85:1 parts by weight.

EXAMPLE 3

117.5 g ( 1.25 mols) of phenol are introduced into a reaction vessel, provided with a stirrer, and thereafter 200 ml of n-butyl acetate are added, after which the stirring device is started and the mixture is warmed to 30° C. 48.8 g of a solution of peracetic acid in butyl acetate are added to this solution of phenol in n-butyl acetate in such a way that the temperature does not exceed 35° C. The solution of the peracetic acid which is added has the following composition: 12.3% by weight of peracetic acid, 1.07% by weight of acetic acid as well as 0.2% by weight of water and 0.15% by weight of hydrogen peroxide. After the temperature has started to fall towards the end of the peracetic acid addition, the mixture is brought to 40° C. and kept at this temperature for 45 minutes, which effects a quantitative peracetic acid conversion. The yield of the dihydroxybenzenes pyrocatechol and hydroquinone is determined by gas chromatography and is 82.7%, relative to the peracetic acid employed. The pyrocatechol selectivity is 56.5%. After distilling off the n-butyl acetate and the acetic acid from the reaction mixture, 109.6 g of phenol are recovered by distillation under 150 mm Hg, which corresponds to a phenol loss of 2.3%, relative to the amount of phenol contained in the two diphenols.

What is claimed is:

1. Process for the preparation of pyrocatechol and hydroquinone by the hydroxylation of phenol, which essentially comprises reacting, a solution which contains less than about 5% by weight of water and less than 2% by weight of hydrogen peroxide, and less than 1% by weight of a free strong acid or of a salt of such acid, of a percarboxylic acid having 1 to 18 carbon atoms in an inert, organic solvent, with phenol at temperatures from −10° C. to 80° C.

2. Process according to claim 1, characterized in that an organic solution of the percarboxylic acid with a content of less than about 1% by weight of water and less than about 1% by weight of hydrogen peroxide is employed.

3. Process according to claim 1, characterized in that an organic solution of the percarboxylic acid with a content of less than 0.5% by weight of water and less than 0.5% by weight of hydrogen peroxide is employed.

4. Process according to claim 1, characterized in that an organic solution of the percarboxylic acid with a content of less than about 0.5% by weight of a strong acid is employed.

5. Process according to claim 1, characterized in that an organic solution of the percarboxylic acid with a content of less than 0.1% by weight of a strong acid is employed.

6. Process according to claim 1, characterized in that the concentration of percarboxylic acid in the organic solution is about 3 to 60% by weight.

7. Process according to claim 1, characterized in that the concentration of percarboxylic acid in the organic solution is about 5 to 50% by weight.

8. Process according to claim 1, characterized in that the concentration of percarboxylic acid in the organic solution is about 10 to 30% by weight.

9. Process according to claim 1, characterized in that the percarboxylic acid in the organic solution contains two to five carbon atoms.

10. Process according to claim 1, characterized in that the percarboxylic acid is perpropionic acid.

11. Process according to claim 1, characterized in that benzene, toluene or dichloropropane is used as the inert organic solvent for the percarboxylic acid.

12. Process according to claim 1, characterized in that benzene is used as the inert organic solvent.

13. Process according to claim 1, characterized in that a percarboxylic acid, the corresponding carboxylic acid of which has a boiling point, under normal pressure, which is at least 30° C. below the boiling point of phenol, is employed.

14. Process according to claim 1, characterized in that a solvent which has a boiling point, under normal pressure, at least 20° C. below that of the carboxylic acid corresponding to the percarboxylic acid, is used as the inert, organic solvent for the percarboxylic acid.

15. Process according to claim 1, characterized in that a solution, which has been obtained by extracting a mixture containing hydrogen peroxide, water, a free strong acid or a salt of such acid as an acid catalyst and the percarboxylic acid with the inert organic solvent, is used as the solution of the percarboxylic acid in an inert organic solvent.

16. Process according to claim 1, characterized in that the reaction between the organic solution of the percarboxylic acid and phenol is carried out at temperatures from about −10° C. to 80° C.

17. Process according to claim 1, characterized in that the reaction between the organic solution of the percarboxylic acid and phenol is carried out at temperatures from about 0° C. to 45° C.

18. Process according to claim 1, characterized in that the reaction between the organic solution of the percarboxylic acid and phenol is carried out at temperatures from about 20° C. to 45° C.

19. Process according to claim 1, characterized in that the phenol being reacted with the organic solution of the percarboxylic acid contains less than 1% by weight of water.

20. Process according to claim 1, characterized in that the carboxylic acid recovered during the working up of the reaction mixture and the solvent recovered during the working up are recycled to the preparation of the organic solution of the percarboxylic acid.

* * * * *

UNITED STATES PATENT AND TRADEMARK OFFICE
CERTIFICATE OF CORRECTION

PATENT NO. : 4,182,917
DATED : January 8, 1980
INVENTOR(S) : Hermann Seifert, et al.

It is certified that error appears in the above-identified patent and that said Letters Patent are hereby corrected as shown below:

Column 3, line 30 delete "," before "R" and delete

" " " before "R" 2nd occurrence.

Column 3, line 44, "azerotropic" should be --azeotropic--.

Column 4, line 56,57 "metanesulphonic" should be --methanesulphonic--.

Column 9, line 52, "insert -- ≙ '' before "1.25".

Signed and Sealed this

Third Day of June 1980

[SEAL]

Attest:

SIDNEY A. DIAMOND

Attesting Officer     Commissioner of Patents and Trademarks